United States Patent [19]

Eubanks et al.

[11] Patent Number: 4,835,285

[45] Date of Patent: May 30, 1989

[54] PROCESSES FOR PREPARING SUBSTITUTED 4-HYDROXYMETHYL-1-PHENYL-3-PYRAZOLIDINONE

[75] Inventors: Robert J. I. Eubanks, Batesville, Ark.; Larry K. Johnson, Kingsport, Tenn.

[73] Assignee: Eastman Kodak Company, Rochester, N.Y.

[21] Appl. No.: 164,662

[22] Filed: Mar. 7, 1988

[51] Int. Cl.[4] .......................................... C07D 207/08
[52] U.S. Cl. .................................................... 548/358
[58] Field of Search ........................................ 548/358

[56] References Cited

U.S. PATENT DOCUMENTS 3,952,009  4/1976  Machiele .................. 548/358
4,000,301  11/1976  Walworth .................. 548/358

FOREIGN PATENT DOCUMENTS 785185   3/1956  United Kingdom ............ 548/358
670571  11/1977  U.S.S.R. .................. 548/358

OTHER PUBLICATIONS

Potts, Kevin T., Comprehensive Heterocyclic Chemistry, 1984, p. 286.

Primary Examiner—Mary C. Lee
Assistant Examiner—J. A. H. Russell
Attorney, Agent, or Firm—Charles R. Martin; William P. Heath, Jr.

[57] ABSTRACT

A process for preparing a substituted 4-hydroxymethyl-1-phenyl-3-pyrazolidinone of the formula

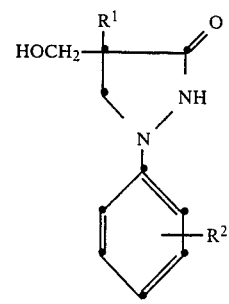

wherein $R^1$ is alkyl and $R^2$ is selected from the group consisting of halogen, alkoxy, nitro, alkyl, and aryl, comprising reacting a cyclic sulfite of the formula

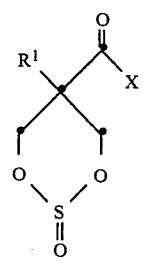

wherein $R^1$ is as described above and X is halide, with an aromatic hydrazine of the formula

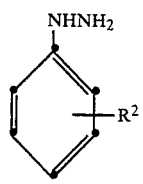

wherein $R^2$ is as described above, in the presence of a basic catalyst and a solvent.

6 Claims, No Drawings

PROCESSES FOR PREPARING SUBSTITUTED 4-HYDROXYMETHYL-1-PHENYL-3-PYRAZOLIDINONE

This invention relates to a process for preparing substituted 4-hydroxymethyl-1-phenyl-3-pyrazolidinones.

1-Aryl-3-pyrazolidinones are oxo-derivatives of pyrazole and have the structural formula:

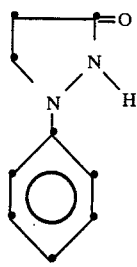

Substituted derivatives of these compounds are well known. One particularly important class of substituted derivatives, 4-hydroxymethyl-1-phenyl-3-pyrazolidinones corresponds to the structure

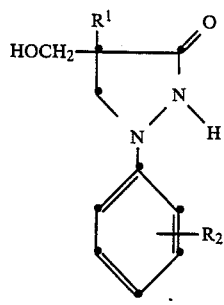

where $R_1$ is alkyl and $R_2$ is selected from the group consisting of halogen, alkoxy, nitro, alkyl and aryl.

The process of this invention provides a method of preparing a substituted 4-hydroxymethyl-1-phenyl-3-pyrazolidinone of the formula

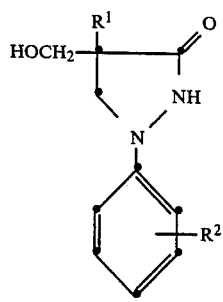

wherein $R^1$ is alkyl, and $R^2$ is selected from the group consisting of halogen, alkoxy, nitro, alkyl, and aryl. This method comprises reacting a cyclic sulfite of the formula

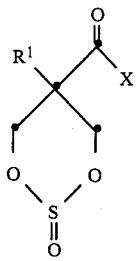

wherein $R^1$ is as described above and X is halide, with an aromatic hydrazine of the formula

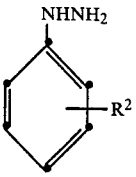

wherein $R^2$ is as defined above. The reaction is conducted in the presence of a basic catalyst and solvent.

The cyclic sulfites used in this process are known in the art and disclosed in U.S. Pat. No. 3,542,856 and U.S. Pat. No. 3,770,770.

The aromatic hydrazines used in this process are also well known in the art. The number of carbon atoms in the alkyl group $R^1$ is in the range of 1 to 12, preferably 1 to 3. The halide X can be chlorine, iodine or bromine but chlorine is preferred. In these compounds $R_2$ can be selected from the group consisting of halogen, alkoxy, nitro, alkyl and aryl. The halogen can be bromo, chloro, iodo, or fluoro. The alkoxy and alkyl group can have 1 to 12, preferably 1 to 3 carbon atoms. The aryl can be benzene, naphthalene, biphenyl or the like which may be further substituted with any substituent which will remain unreacted and will not interfere with the reaction.

The process of this invention is preferably conducted at a temperature of about 25° to 100° C., and more preferably at about 40° to 70° C. The reaction is typically conducted at atmospheric pressure, although other pressures may also be employed. Under these conditions, the reaction is typically completed in a period of time of less than about 10 minutes, and very often less than 5 minutes.

The solvent useful in this reaction can be any solvent which results in preparation of the desired product. Examples of suitable solvents are polar hydrocarbons, hydrocarbon halides and alkyl or aryl ethers. Other suitable solvents may be used.

The catalyst useful in this reaction can be any material which are basic and enhances the rate of preparation of product. Examples of suitable catalysts are sodium bicarbonate, sodium hydroxide, pyridine and benzyltrialkylammonium chloride. Other basic catalysts known in the art may also be utilized.

The substituted 4-hydroxymethyl-1-phenyl-3-pyrazolidinones prepared by the process of this invention are useful as silver halide developers in the photography field.

EXAMPLE 1

Preparation of 4-Hydroxymethyl-4-Methyl-1-Phenyl-3-Pyrazolidinone

A mixture of 0.163 kg (1.5 mol) phenylhydrazine, 0.630 kg (7.5 mol) sodium bicarbonate, 0.75 L toluene, 75 mL of water and 3.0 g (0.013 mol) benzyl triethylammonium chloride heated to and maintained at 60° to 70° C. while 0.466 kg (ca 2.05 mol) of 1-methyl-4-oxo-3,5-dioxa-4-thiocyclohexane carbonyl chloride are added over a period of four hours. The reaction mixture is held at 70° C. for 1 hour, and 1.5 L of water added. The reaction mixture is then heated to 80° C. and held for one additional hour at this temperature before the lower aqueous phase is decanted. Residual water is then removed by azeotropic distillation, 0.120 L of isopropanol are added at 70° C., and crystallization is induced by cooling to 0° to 5° C. The product is isolated by filtration, washed with two 0.1 L 0° to 5° C. toluene washes, and dried in a 70° C. forced-air oven overnight. Approximately 0.229 kg (1.11 mol, 74% of theoretical amount) of 4-hydroxymethyl-4-methyl-1-phenyl-3-pyrozolidinone is isolated. The IR and NMR(H) spectra match those of this compound, M.P.: 121.8° to 123.3° C.

The invention now having been fully described, it will be apparent to one of ordinary skill in the art that many changes and modifications can be made thereto without departing from the spirit or scope of the invention as set forth herein.

What is claimed is:

1. A process for preparing a substituted 4-hydroxymethyl-1-phenyl-3-pyrazolidinone of the formula

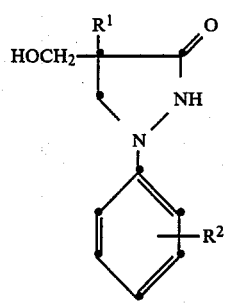

wherein $R^1$ is alkyl containing 1 to 3 carbon atoms and $R^2$ is selected from the group consisting of halogen, alkoxy containing 1 to 3 carbon atoms, nitro, alkyl containing 1 to 3 carbon atoms, and aryl selected from the group consisting of benzene, naphthalene or biphenyl, comprising reacting a cyclic sulfite of the formula

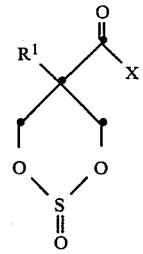

wherein $R^1$ is as described above and X is halide, with an aromatic hydrazine of the formula

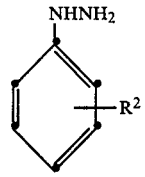

wherein $R^2$ is as described above, in the presence of a basic catalyst and a solvent.

2. The process of claim 1 wherein the reaction is conducted at a temperature of 25° to 100° C.

3. The process of claim 2 wherein the reaction is conducted at a temperature of 40° to 70° C.

4. The process of claim 1 wherein the basic catalyst is sodium bicarbonate.

5. The process of claim 1, wherein the solvent is selected from the group consisting of polar hydrocarbons, hydrocarbon halides and alkyl or aryl ethers.

6. A process for preparing 4-hydroxy-4-methyl-1-phenyl-3-pyrazolidinone corresponding to the formula

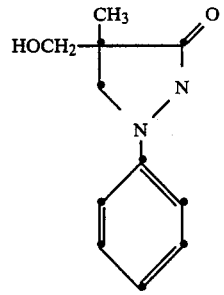

comprising reacting a cyclic sulfite of the formula

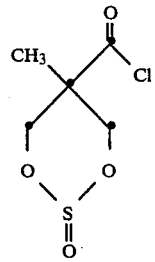

with an aromatic hydrazine of the formula

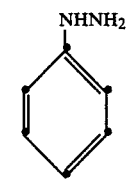

in the presence of a basic catalyst and a solvent at a temperature of about 40° C. to 70° C.

* * * * *